United States Patent [19]

Schultz

[11] Patent Number: 4,626,971
[45] Date of Patent: Dec. 2, 1986

[54] ILLUMINATED SURGICAL TRAY APPARATUS

[76] Inventor: Pamela J. Schultz, 2332 S. 10th Ave., Broadview, Ill. 60153

[21] Appl. No.: 735,272

[22] Filed: May 17, 1985

[51] Int. Cl.[4] .................. F21V 33/00; G02B 27/02
[52] U.S. Cl. .................................... 362/154; 206/557; 206/370; 350/238; 350/243
[58] Field of Search ............... 362/33, 97, 109, 120, 362/125, 138, 143, 154, 257, 311; 206/557, 370; 269/16; 350/235, 238, 239, 243, 246

[56] References Cited

U.S. PATENT DOCUMENTS

| 467,630 | 1/1892 | Roland | 350/244 |
|---|---|---|---|
| 2,435,741 | 2/1948 | Fleener | 350/239 |
| 2,563,315 | 8/1951 | Den Uyl | 132/73.5 |
| 2,713,807 | 7/1955 | Herbert | 350/238 |
| 2,812,422 | 11/1957 | Provi | 177/177 |
| 2,903,129 | 9/1959 | Anderson | 206/363 |
| 3,247,757 | 4/1966 | Callaghan | 350/243 X |
| 3,437,423 | 4/1969 | Mondiadis | 206/557 X |
| 3,774,993 | 11/1973 | Senff | 350/243 |
| 4,011,944 | 3/1977 | Cooley et al. | 206/557 |
| 4,030,814 | 6/1977 | Clifton et al. | 350/239 X |
| 4,071,883 | 1/1978 | Dennis | 362/97 |
| 4,254,452 | 3/1981 | Switala | 362/154 |
| 4,540,239 | 9/1985 | Frankel | 350/235 |

Primary Examiner—Willis R. Wolfe, Jr.
Attorney, Agent, or Firm—Dick and Harris

[57] ABSTRACT

An illuminated surgical tray apparatus for the facilitated viewing and selection of thin fibrous surgical materials, such as sutures and related instruments, during a surgical procedure. The apparatus includes a light source, viewing lens and optically colored contrasting disclosure field or background for enhancing the visibility of the objects positioned within the interior of the apparatus. The surgical tray apparatus further possesses a substantially air, water and steam-tight, fireproof light construction, together with curved edges and corners to facilitate sterilization of the overall device and shrink wrapping thereof to maintain its sterilized nature.

16 Claims, 5 Drawing Figures

ILLUMINATED SURGICAL TRAY APPARATUS

BACKGROUND OF THE INVENTION

The present invention relates in general to surgical procedure implements and in particular to an illuminated surgical tray apparatus for the facilitated viewing and selection of thin fibrous surgical materials such as sutures and related instruments associated therewith, in a sterile operating room environment.

With conventional surgery techniques and procedures, suture materials have become increasingly thin and difficult to inspect by the naked eye of a nurse or surgeon attending the procedure. Actual surgical needles carrying a "threaded" suture, threaders themselves and minute strands of suture material are not easily resolvable by the human eye—resulting in potentially costly time delays to recheck for such suture materials. Few if any devices are presently known to address the particular disclosure of suture material in a surgical environment.

While surgical disclosure trays for sutures are not known to exist, various other "magnifying" apparata such as Roland, U.S. Pat. No. 467, 630 and Fleenor, U.S. Pat. No. 2,435,741 have combined tongs or tweezers with magnifying lenses. Den Uyl, U.S. Pat. No. 2,563,315 and Senff, U.S. Pat. No. 3,774,993 have employed magnifying lenses with bottom trays. Other devices such as Callaghan, U.S. Pat. No. 3,247,757 have employed a substantially closed box-like structure for viewing and turning coins and having a "built-in" magnifying lens and light source. Herbert, U.S. Pat. No. 2,713,807 employs a lower tray, light source and magnifying lens; while Dennis, U.S. Pat. No. 4,071,883 employs a light box, lit from below, and having a light absorbing or reflective background.

Drawbacks have additionally been encountered with present surgical trays as well as the above-described prior art and conventional "magnifier" construction. In particular, a conventional surgical tray can present problems in firstly locating and then selecting minute thread-like surgical sutures and the like, in an operating room environment since virtually few, if any, features have been integrated into such trays towards expressly disclosing suture material.

It is thus an object of the present invention to provide an improved illuminated surgical tray apparatus that serves to enhance the visibility of minute objects such as sutures positioned therein, through the use of a focused light source and an optically colored, optical disclosure field means.

It is further an object of the present invention to provide a construction for the surgical tray apparatus that facilitates access to the interior thereof, for insertion and removal of objects therefrom.

It is additionally an object of the present invention to provide a substantially sealed light construction that is air, water and steam tight so as to enable autoclaving of the overall apparatus so as to enable use and reuse thereof in a sterile operating room environment. Alternatively, such a construction will preclude sparks or fires, while additionally enabling other sterilization techniques such as ethylene oxide sterilization.

It is yet another object of the present invention to provide a non-glare optical disclosure field material that serves to maintain the minute objects placed thereon and to provide a substantially rounded edge and corner construction that facilitates puncture-proof shrink wrapping of the entire apparatus, so as to maintain its sterility—in a construction that can be manufactured at a minimum cost and effort.

These and other objects of the invention will become apparent in light of the present specification, drawings and claims.

SUMMARY OF THE INVENTION

The present invention comprises an illuminated surgical tray apparatus for the facilitated viewing and selection of thin fibrous surgical materials such as sutures and related instruments associated therewith, in a substantially sterile operating room environment. The apparatus comprises a substantially flat tray support means capable of accommodating one or more ones of the suture material and the related surgical instruments thereon. The flat tray support means has a front side and a rear side, with front plate means being operably attached along the front plate attachment region to the front side of the flat tray support means and emanating substantially upwardly therefrom. The front plate means has a top portion and a bottom portion with viewing means operably contained therewithin, so as to facilitate viewing of the materials and related items positioned thereon. Optical disclosure field means are operably associated with the flat tray support means and the viewing means so as to provide a visually contrasting background to, in turn, further facilitate viewing of the materials and related items positioned upon the support means.

Lighting means are operably associated with the support means so as to illuminate the materials and related items positioned upon the optical field means. The lighting means is further, preferably and operably affixed to the front plate means. The top of the front plate means and the rear side of the support means describe an insertion region for alternative placement of the materials and related items on this disclosure field, as well as for removal therefrom. The above lighting means, viewing means, support means and optical disclosure field means cooperate so as to provide improved resolution and, in turn, facilitated viewing of, access to and selection of the instruments and related items positioned within the apparatus.

One preferred embodiment of the illuminated surgical tray apparatus of the present invention, further comprises rear plate means operably attached to the rear side of the flat tray support means along a rear plate attachment region and further having a top side and a bottom side. In this embodiment, the optical disclosure field means extends substantially from the top of the rear plate means to the bottom of the front plate means. The optical disclosure field means is substantially continuous from the top of the rear plate means to the bottom of the front plate means for facilitated elevated viewing of the supported materials and related items positioned upon the flat tray support in the interior of the device.

In the preferred embodiment of the invention, the front plate means, the support tray means and the rear plate means are operably configured so as to provide a substantially U-shaped cross-sectional configuration for the apparatus. Additionally, the front plate attachment region and the rear plate attachment region are substantially curvilinear in shape so as to facilitate shrink wrapping of the apparatus—without inadvertent piercing of the shrink-wrap material.

The lighting means of the preferred embodiment of the present invention is focused substantially downwardly upon the optical disclosure field means and is operably positioned proximate to the top side of the front plate means.

The lighting means further comprises bulb means extending substantially across the entire width of the front plate means, socket means operably associated with the bulb means, power means operably associated with the bulb means and the socket means so as to power the bulb for illumination and switch means operably associated with the power means so as to enable alternative activation and deactivation of the bulb means for selective illumination of the support tray means.

The switch means in the preferred embodiment are substantially sealed, in water-steam-tight fashion, so as to facilitate sterilization of the overall apparatus through either autoclaving (with for example, autoclavable materials) or through ethylene oxide or other sterilization techniques. Reflector means positioned substantially behind the bulb means serve to enhance the illumination of the support means by the lighting means. Lighting enclosure means substantially surround the bulb means, socket means and the power means, (cooperating with the switch means) so as to provide a substantially water and steam tight housing to the lighting means in order to further enable the sterilization of the apparatus from repeated surgical usage as well as to limit sparks or potential for fire therefrom. The enclosure means are substantially transparent to enable the transmission of light therethrough.

The invention further comprises the lighting means being operably affixed proximate the top portion of the front plate, in a position above the viewing means, and extending across the width of the apparatus. The viewing means comprises a substantially upwardly extending lens member positioned in the front plate means with the lens member extending from a position substantially adjacent the front plate attachment region to a position proximate to the top of the front plate means. The lens member comprises, in the preferred embodiment of the invention, a magnifying lens operably integrated into the front plate means.

The optical disclosure field means of the present invention preferably comprises a single layer of substantially opaque, colored material continuously extending from the front plate attachment region across the entire width and depth of the support tray means as well as across the entire width and height of the back plate means. The layer of colored material is further substantially depressible to facilitate the tactile grasping of the materials and instruments placed thereon and otherwise serving to restrain the positions of same, as placed thereon. The layer of colored material may, for example, comprise a substantially felt-like material or alternatively, can comprise a substantially foam-like fibrous vinyl material. The color of the layer of colored material in the preferred embodiment is yellow.

DETAILED DESCRIPTION OF THE DRAWINGS

Figure 1:
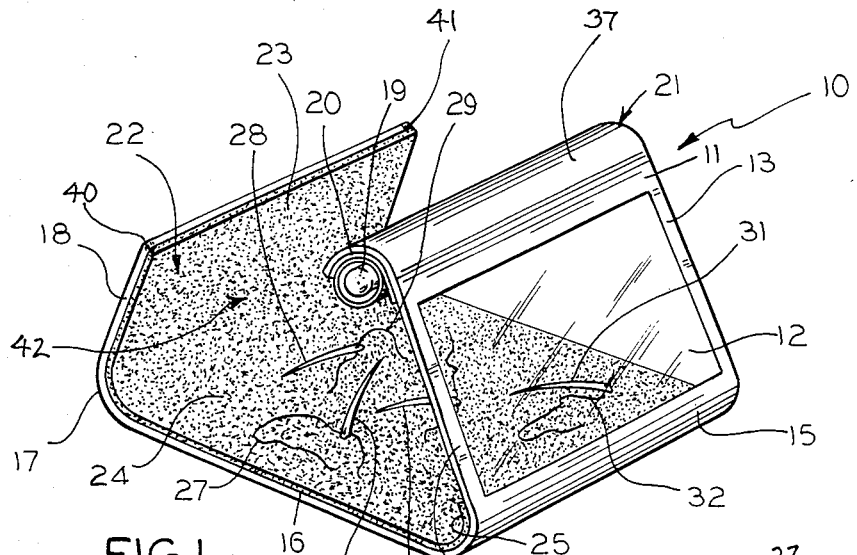
FIG. 1 is a top right perspective view of the lighted surgical tray apparatus showing its sealed lighting configuration, front plate with magnifying lens, bottom support tray, back plate, rounded edges and surgical sutures, instruments and related items positioned upon the support tray and optical disclosure field.

While this invention is susceptible of embodiment in many different forms, there is shown in the drawings and will herein be described in detail, one specific embodiment, with the understanding that the present disclosure is to be considered as an exemplification of the principles of the invention and is not intended to limit the invention to the embodiment illustrated.

The preferred embodiment of the invention is shown in FIGS. 1 through 5, in which FIG. 1 shows the 3-sided and substantially U-shaped configuration of illuminated surgical tray apparatus 10 having inclined front plate 13. Front plate 13 houses viewing lens 12 positioned in front of substantially flat bottom support tray surface 16 and upwardly extending back plate 18. An optical disclosure field 22 is thus formed with overhead lighting assembly 21 capable of illuminating same and defining an insertion region 42 in apparatus 10 through which suture articles can be positioned or removed. Also shown in FIG. 1 are lighting assembly reflector 20 and light bulb 19.

Surgical needles 26, 28, 30 and 31 as well as sutures 27, 29 and 32 are, by way of FIG. 1, shown positioned on top of optical disclosure field 22 and thus upon substantially flat, bottom tray support 16 of surgical tray 10. Front plate 13 is attached to bottom support tray 16, in the preferred embodiment, along curved attachment region 15, proximate the bottom of front plate 13 and the front portion of tray 16. Back plate 18 is also attached to tray 16, along curved attachment region 17 proximate its bottom portion, and the rear portion of tray 16.

Preferably, edges 15, 17 and 37 and corners 40 and 41 of surgical tray 10 are substantially rounded, so as to facilitate the enclosing or wrapping of the device by shrink wrapping materials and techniques. In this preferred embodiment, lighting assembly 21 is attached to viewing means 11 and in particular inclined front plate 13 at the rounded top portion 37, thereof. Substantially transparent viewing lens 12, preferably of the magnifying type, may be integrally framed by border 14 of inclined front plate 13 or remain unframed on its sides.

Figure 2:
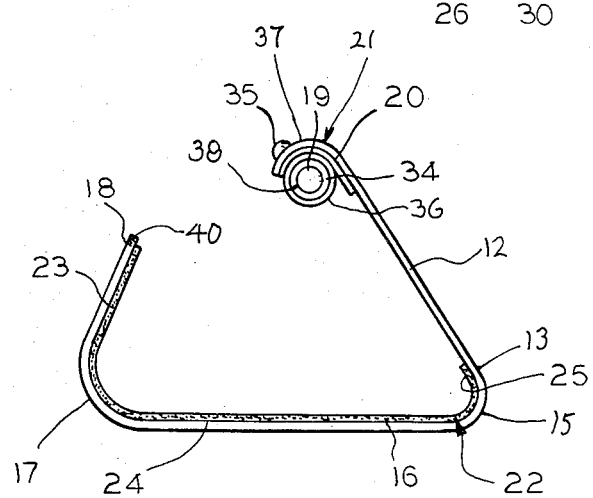
FIG. 2 is an elevated side view of the substantially U-shaped lighted surgical tray apparatus as viewed from the left, showing the sealed lighting configuration, front plate with magnifying lens, curved edged construction, bottom support tray, back plate and optical disclosure field positioned thereon.

As also shown in FIG. 1, three-sided surgical tray apparatus 10 is open at the left, right and top sides (and as viewed in FIG. 2), in the preferred embodiment, to facilitate access to interior portions of apparatus 10 and in particular, insertion region 42, for placement or removal of surgical instruments and related items, such as suture articles 26 through 32 placed upon bottom tray support 16 and optical disclosure field bottom portion 24. FIG. 2 further shows the open top and open sided construction of surgical tray 10 of the preferred embodiment and further illustrates the substantially U-shaped cross-sectional configuration thereof towards defining insertion region 42.

As shown in FIGS. 1 and 2, lighting means 21 includes bulb 19 and curved reflector 20 positioned about its periphery to enhance the illumination provided by bulb 19 and focus same downwardly onto optical disclosure field means 24. Switch 35 is also provided, operably connected to socket 34 and power source 40 so as to enable selective activation and deactivation of lighting means 21 and in particular bulb 19 for illumination.

Power source 50 in the preferred embodiment comprises two self-contained standard DC batteries arranged in series, though in alternative embodiments of the present invention, the substitution of other DC or AC power sources, are to be considered as falling within the scope of the present invention.

As also shown in FIGS. 1 and 2, are continuous optical disclosure field means 22, in the preferred embodiment includes: disclosure field back portion 23 extending the width of and covering the interior of inclined, upwardly extending back plate 18; disclosure field bottom portion 24 likewise spanning the width of and covering bottom support tray surface 16; and disclosure field front portion 25 extending up a portion of front plate 13 to approximately the bottom edge of viewing lens 12. In the preferred embodiment, optical disclosure field means 23 is a continuous sheet of non-glare, opaque yellow colored, substantially fibrous (felt-like or plastic foam-like) textured material in order to provide a surface that maintains the position of objects placed thereon, that yields on touch to facilitate grasping of an article and that provides a non-slippery, contrasting visual background that serves to highlight surgical instruments and small objects (such as surgical sutures) positioned thereon, thereby facilitating the viewing positioning and selection thereof. The optical disclosure means 22 is securely, yet detachably affixed to apparatus 10 and alternative colors, materials, textures or configurations of optical disclosure field means 22 should also be considered as being within the scope of the present invention.

Lighting means 21 extends substantially along the entire width of apparatus 10 and is positioned in an overhead position with respect to bottom support surface 16 so as to evenly and fully illuminate any objects positioned thereon. Lighting means 21 further includes enclosure 36 surrounding bulb 19, socket 37 and power source 40. Moreover, in the preferred embodiment, switch 35 is a sealed bubble-type or push-bottom type switch positioned on the interior side of rounded edge top portion 37 of front plate 13.

In the preferred embodiment, power source 50 consists of batteries included in sealed enclosure 36, so as to provide a substantially sealed lighting assembly 21, thereby making apparatus 10 sterilizable, and spark and fire resistant. Enclosure 36 is detachable from top rounded edge portion 37 of front wall 13 and further includes removable end caps 38 to facilitate access to bulb 19, for replacement thereof.

Figure 3:
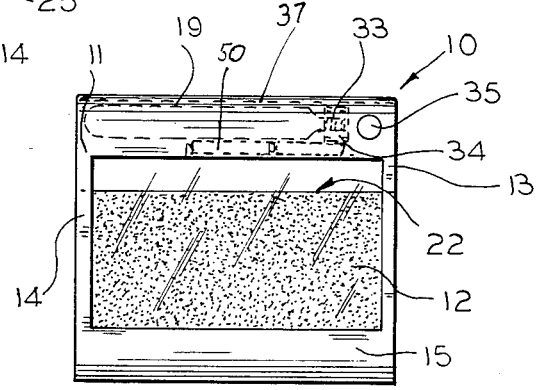
FIG. 3 is an elevated front view of the lighted surgical tray apparatus showing the front plate and viewing lens formed therein, as well as its overhead sealed lighting configuration, back plate and optical disclosure field.

FIG. 3 shows apparatus 10 as comprising viewing means 11, front plate 13, and viewing lens 12 formed therein and surrounded by frame 14. Shown in phantom are bulb 19, socket 34, switch 35 and power source 50 positioned proximate top rounded portion 37 of inclined front plate 13. Optical disclosure field 22, and particularly, back portion 23 affixed to back plate 18, and bottom portion 24, affixed to bottom tray surface 16, is visible through viewing lens 12, so as to facilitate elevated viewing of the objects positioned within the interior of apparatus 10.

In the preferred embodiment of the present invention, viewing lens 12 is a transparent magnifying lens, so as to facilitate the viewing and selection of the desired surgical instrument or minute sutures, and the like, located on disclosure field 22. Viewing means 11 is inclined at an angle which optimizes viewing of the objects positioned on the interior of surgical tray apparatus 10 from above, since when in use in an operating room setting, tray apparatus 10 will usually be positioned immediately below the eye level of the person using the tray. Optical disclosure field 22 extends to and covers the interior surface of inclined, upwardly extending back plate 18 so as to provide an enhanced illuminated background to increase the visibility of instruments and other objects positioned within tray apparatus 10 and avoid glare or other visual distractions.

Figure 4:
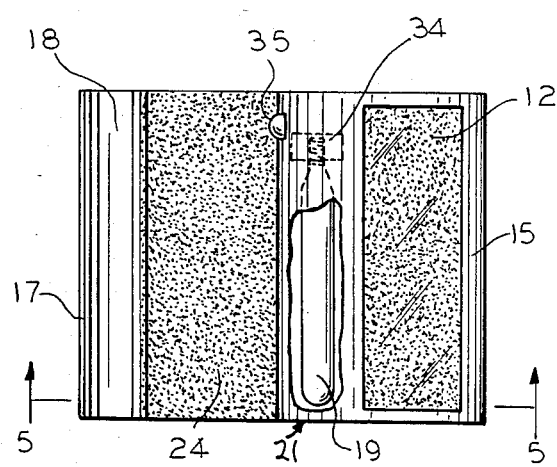
FIG. 4 is a top plan view of the lighted surgical tray apparatus of FIGS. 1 through 3 showing its optical disclosure field, front plate with viewing lens, sealed lighting assembly, bottom tray support and back plate.

FIG. 4 additionally shows surgical tray apparatus 10, a back plate 18, and inclined front plate 13 having viewing lens 12 built into it. Also shown are overhead lighting means 21, including light bulb 19, socket 34 and switch 35, as affixed to socket 34, which leads to power source 50. Optical disclosure field bottom portion 24 is also visible through the substantially open, top portion of apparatus 10 as well as through viewing lens 12. As seen in FIGS. 2 and 4, the substantially open top and side provide substantially unencumbered access to the interior insertion region 42 of tray 10.

Figure 5:
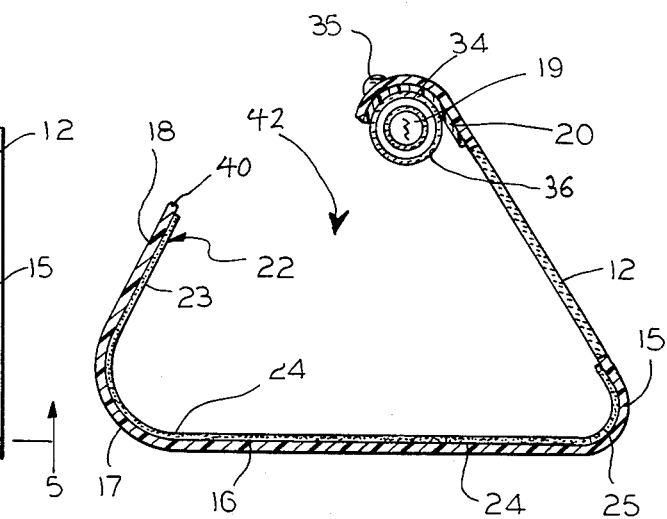
FIG. 5 is a cross-sectional view of the apparatus of FIG. 4 taken along lines 5—5 and looking in the direction of the arrows, showing its overhead lighting assembly, front plate, bottom tray support, back plate and optical disclosure field thereon.

In FIG. 5, optical disclosure field 22 is shown spanning the interior of apparatus 10, and in particular, back portion 23 covering back plate 18, bottom portion 24 covering bottom support tray 16 and front plate 25 covering the interior of attachment region 15 of front plate 13.

In operation, surgical instruments and the like, such as surgical needles 26, 28, 30 and 31 and sutures 27, 29 and 32 are placed upon bottom optical disclosure field surface 24 covering bottom support tray surface 16, in the interior of surgical tray apparatus 10. Lighting means 21 is then activated so as to illuminate the interior of apparatus 10, and in particular bottom support surface 16, by depressing switch 35 which in turn causes power source 40 to supply electrical current to light bulb 19, thereby illuminating bulb 19 with reflector 20 focusing the light down into insertion region 42 of apparatus 10; and onto surface 24.

Depressing switch 35 a subsequent time serves to deactivate lighting means 10. It is contemplated that, in ordinary operation, apparatus 10 is orientated so as to face the user thereof at an elevation below eye level, so that the user can see through viewing lens 12 from in front and above to see substantially all of bottom support surface 24 bearing the surgical instruments and related items. Viewing lens 12, in the preferred embodiment, serves to magnify the appearance of the items positioned in the interior of apparatus 10 so as to facilitate selection and removal of the desired items. Lens 12 and inclined front plate 13 are further configured so as to minimize the likelihood of parallax and other visual distortion.

Optical disclosure field 22 serves as an opaque, yellow colored, textured background that keeps the surgical instruments and related minute items such as sutures in place, while providing a non-glare contrasting background that makes it easier to see such objects when viewed through lens 12. The portion of disclosure field 22 covering back plate 18, results in a similar, uniformly opaque, non-glare background so as to further facilitate the viewing of the surgical instruments through lens 12 when slightly elevated by a nurse or surgeon. Access to insertion region 42 for positioning or removing objects from within apparatus 10 is provided by the substantially open top, left and right sides of apparatus 10.

Due to the substantially sealed nature of sparkproof, fire resistant lighting assembly 21 including switch 35, surgical tray apparatus 10 may be sterilized in an autoclave or sterilized by ethylene oxide techniques. Rounded edges 15, 17 and 37 and rounded corners 40 and 41, in the preferred embodiment, facilitate the shrink wrapping of apparatus 10 to maintain the sterilized nature thereof. Accordingly, apparatus 10 can be used and reused without contaminating the "sterile field" of an operating room environment.

The foregoing description and drawings merely explain and illustrate the invention. The invention is not limited thereto, except insofar as the appended claims are so limited, as those skilled in the art who have the disclosure before them will be able to make modifications and variations therein without departing from the scope of the invention.

What is claimed is:

1. An illuminated surgical tray apparatus for the facilitated viewing and selection of thin fibrous surgical materials such as suture materials and surgical instruments associated therewith, in a sterile operating room environment, said apparatus comprising:

substantially flat tray support means capable of accommodating said suture material and said surgical instruments thereon;

said flat tray support means having a front side and a rear side;

front plate means operably attached along a front plate attachment region to the front side of said flat tray support means and emanating substantially upwardly therefrom;

said front plate means having a top portion and a bottom portion;

viewing means operably contained within said front plate means so as to facilitate viewing of said suture material and said surgical instruments positioned thereon;

optical disclosure field means operably associated with said flat tray support means and said viewing means to provide a visually contrasting background so as to facilitate viewing of said suture material and surgical instruments positioned upon said support means;

lighting means operably associated with said support means so as to illuminate said suture material and surgical instruments positioned upon said optical field means;

said lighting means being operably affixed to said front plate means;

said top of said front plate means and said rear side of said support means describing an insertion region for alternative placement of said suture material and said surgical instruments on said disclosure field and removal therefrom;

said lighting means, viewing means, support means and optical disclosure field means cooperating so as to provide facilitated viewing of access to and selection of said suture material and said surgical instruments positioned within said apparatus;

rear plate means operably attached to said rear side of said flat tray support means along a rear plate attachment region of said rear plate means;

said rear plate means extending substantially upwardly therefrom and having a top side and a bottom side;

said optical disclosure field means extending substantially from said top of said rear plate means to the bottom of said front plate means; and said optical disclosure field means being substantially continuous from said top of said rear plate means to said bottom of said front plate means, for facilitated elevated viewing of said suture material and said surgical instruments positioned upon said flat tray support means.

2. An illuminated surgical tray apparatus for the facilitated viewing and selection of thin fibrous surgical materials such as suture material and surgical instruments associated therewith, in a sterile operating room environment, said apparatus comprising:

substantially flat tray support means capable of accommodating said suture material and said surgical instruments thereon;

said flat tray support means having a front side and a rear side;

front plate means operably attached along a front plate attachment region to the front side of said flat tray support means and emanating substantially upwardly therefrom;

said front plate means having a top portion and a bottom portion;

viewing means operably contained within said front plate means so as to facilitate viewing of said suture material and said surgical instruments positioned thereon;

optical disclosure field means operably associated with said flat tray support means and said viewing means to provide a visually contrasting background so as to facilitate viewing of said suture material and surgical instruments positioned upon said support means;

lighting means operably associated with said support means so as to illuminate said suture material and surgical instruments positioned upon said optical field means;

said lighting means being operably affixed to said front plate means;

said top of said front plate means and said rear side of said support means describing an insertion region for alternative placement of said suture material and surgical instruments on said disclosure field and removal therefrom;

said lighting means, viewing means, support means and optical disclosure field means cooperating so as to provide facilitated viewing of access to and selection of said suture material and surgical instruments positioned within said apparatus;

rear plate means operably attached to said rear side of said flat tray support means along a rear plate attachment region of said rear plate means;

said rear plate means extending substantially upwardly therefrom and having a top side and a bottom side; and said front plate means, said support tray means and sad rear plate means being operably configured so as to provide a substantially U-shaped cross-sectional configuration.

3. An illuminated surgical tray apparatus for the facilitated viewing and selection of thin fibrous surgical materials such as suture material and surgical instruments associated therewith, in a sterile operating room environment, said apparatus comprising:

substantially flat tray support means capable of accommodating said suture material and said surgical instruments thereon;

said flat tray support means having a front side and a rear side;

front plate means operably attached along a front plate attachment region to the front side of said flat tray support means and emanating substantially upwardly therefrom;

said front plate means having a top portion and a bottom portion;

viewing means operably contained within said front plate means so as to facilitate viewing of said suture material and said surgical instruments positioned thereon;

optical disclosure field means operably associated with said flat tray support means and said viewing means to provide a visually contrasting background so as to facilitate viewing of said suture material and surgical instruments positioned upon said support means;

lighting means operably associated with said support means so as to illuminate said suture material and surgical instruments positioned upon said optical field means;

said lighting means being operably affixed to said front plate means;

said top of said front plate means and said rear side of said support means describing an insertion region for alternative placement of said suture material and surgical instruments on said disclosure field and removal therefrom;

said lighting means, viewing means, support means and optical disclosure field means cooperating so as to provide facilitated viewing of access to and selection of said suture material and surgical instruments positioned within said apparatus;

rear plate means operably attached to said rear side of said flat tray support means along a rear plate attachment region of said rear plate means;

said rear plate means extending substantially upwardly therefrom and having a top side and a bottom side; and said front plate attachment region and said rear plate attachment region being substantially curvilinear in shape so as to facilitate puncture resistant shrink wrapping of said apparatus.

4. An illuminated surgical tray apparatus for the facilitated viewing and selection of thin fibrous surgical materials such as suture material and surgical instruments associated therewith, in a sterile operating room environment, said apparatus comprising:

substantially flat tray support means capable of accommodating said suture material and said surgical instruments thereon;

said flat tray support means having a front side and a rear side;

front plate means operably attached along a front plate attachment region to the front side of said flat tray support means and emanating substantially upwardly therefrom;

said front plate means having a top portion and a bottom portion;

viewing means operably contained within said front plate means so as to facilitate viewing of said suture material and said surgical instruments positioned thereon;

optical disclosure field means operably associated with said flat tray support means and said viewing means to provide a visually contrasting background so as to facilitate viewing of said suture material and surgical instruments positioned upon said support means;

lighting means operably associated with said support means so as to illuminate said suture material and surgical instruments positioned upon said optical field means;

said lighting means being operably affixed to said front plate means;

said top of said front plate means and said rear side of said support means describing an insertion region for alternative placement of said suture material and surgical instruments on said disclosure field and removal therefrom;

said lighting means, viewing means, support means and optical disclosure field means cooperating so as to provide facilitated viewing of access to and selection of said suture material and surgical instruments positioned within said apparatus;

said lighting means further comprising bulb means;

said bulb means extending across substantially the width of said front plate means;

socket means operably associated with said bulb means;

power means operably associated with said bulb means and said socket means so as to power said bulb for illumination;

switch means operably associated with said power means so as to enable selective activation and deactivation of said bulb means for selective illumination of said support tray means;

said switch means being substantially sealed so as to enable the sterilization of said overall apparatus while reducing potential for inadvertent sparking or fires by said lighting means;

reflector means substantially surrounding said bulb means so as to prompt a downward illumination of said support means by said lighting means;

lighting enclosure means substantially surrounding all of said bulb means, socket means, and power means and cooperating with said switch means, so as to provide a substantially water and steam tight housing to same, to enable the autoclaving of said apparatus for repeated surgical usage; and said enclosure means being substantially transparent to enable the transmission of light therethrough.

5. An illuminated surgical tray apparatus for the facilitated viewing and selection of thin fibrous surgical materials such as suture material and surgical instruments associated therewith, in a sterile operating room environment, said apparatus comprising:

substantially flat tray support means capable of accommodating said suture material and said surgical instruments thereon;
said flat tray support means having a front side and a rear side;
front plate means operably attached along a front plate attachment region to the front side of said flat tray support means and emanating substantially upwardly therefrom;
said front plate means having a top portion and a bottom portion;
viewing means operably contained within said front plate means so as to facilitate viewing of said suture material and said surgical instruments positioned thereon;
optical disclosure field means operably associated with said flat tray support means and said viewing means to provide a visually contrasting background so as to facilitate viewing of said suture material and said surgical instruments positioned upon said support means;
lighting means operably associated with said support means so as to illuminate said surgical material and said surgical instruments positioned upon said optical field means;
said lighting means being operably affixed to said front plate means;
said top of said front plate means and said rear side of said support means describing an insertion region for alternative placement of said suture material and said surgical instruments on said disclosure field and removal therefrom;
said lighting means, viewing means, support means and optical disclosure field means cooperating so as to provide facilitated viewing of, access to and selection of said suture material and surgical instruments positioned within said apparatus;
rear plate means operably attached to said rear side of said flat tray support means along a rear plate attachment region of said rear plate means;
said rear plate means extending substantially upwardly therefrom and having a top side and a bottom side;
said optical disclosure field means comprising:
  a single layer of substantially opaque, contrastingly colored material continuously extending from said front plate attachment region across the entire width and depth of said support tray means as well as across the entire width and height of said back plate means; and
  said layer of colored material being substantially depressible to facilitate the tactile grasp of said suture material and surgical instruments, and otherwise restraining the positions of same as placed thereon.

6. The apparatus as recited in claim 5 wherein said layer of contrastingly colored material comprises a substantially felt-like material.

7. The apparatus as recited in claim 5, wherein said layer of contrastingly colored material comprises a substantially foam-like material.

8. The apparatus as recited in claim 5 wherein the color of said contrastingly colored material is yellow.

9. An illuminated surgical tray apparatus for the facilitated viewing and selection of thin fibrous surgical materials such as suture material and surgical instruments associated therewith, in a sterile operating room environment, said apparatus comprising:

substantially flat tray support means capable of accommodating said suture material and said surgical instruments thereon;
said flat tray support means having a front side and a rear side;
front plate means operably attached along a front plate attachment region to the front side of said flat tray support means and emanating substantially upwardly therefrom;
said front plate means having a top portion and a bottom portion;
viewing means operably contained within said front plate means so as to facilitate viewing of said suture material and said surgical instruments positioned thereon;
optical disclosure field means operably associated with said flat tray support means and said viewing means to provide a visually contrasting background with respect to said suture material and surgical instruments so as to facilitate viewing of said suture material and surgical instruments positioned upon said support means and differentiate said suture material and surgical instruments therefrom in said operating room environment;
lighting means operably associated with said support means so as to illuminate said suture material and surgical instruments positioned upon said optical disclosure field means and said visually contrasting background;
said lighting means being operably affixed to said front plate means;
said top of said front plate means and said rear side of said support means describing an insertion region for alternative placement of said suture material and surgical instruments on said disclosure field and removal therefrom; and
said lighting means, viewing means, support means and optical disclosure field means cooperating so as to provide facilitated viewing of, by positioning a visually contrasting background with, access to and selection of said suture material and surgical instruments positioned within said apparatus.

10. The apparatus as recited in claim 9 wherein said lighting means is focused substantially downwardly upon said optical disclosure field means.

11. The illuminated surgical tray apparatus according to claim 9 wherein the invention further comprises:
rear plate means operably attached to said rear side of said flat tray support means along a rear plate attachment region of said rear plate means; and
said rear plate means extending substantially upwardly therefrom and having a top side and a bottom side.

12. The apparatus as recited in claim 11 wherein said optical disclosure field means and said visually contrasting background extends substantially from said top of said rear plate means to the bottom of said front plate means.

13. The apparatus as recited in claim 9 wherein said lighting means is operably positioned proximate to said top side of said front plate means.

14. The apparatus as recited in claim 13 wherein said invention further comprises said lighting means being operably affixed proximate said top side of said front plate means in a position above said viewing means, and extending substantially across the entire width of the apparatus.

15. The apparatus as recited in claim 9 wherein said viewing means comprises:
   a substantially upwardly extending lens member positioned in said front plate means; and
   said lens member extending from a position substantially adjacent said front plate attachment region to a position proximate to the top of said front plate means.

16. The apparatus as recited in claim 15 wherein said lens member comprises a magnifying lens operably affixed to said front plate means.

* * * * *